(12) United States Patent
Ross et al.

(10) Patent No.: US 6,833,150 B1
(45) Date of Patent: Dec. 21, 2004

(54) SPRAY-DRIED BACTERIOCIN POWDER WITH ANTI-MICROBIAL ACTIVITY

(75) Inventors: Reynolds Paul Ross, Cork (IE); Colin Hill, Cork (IE)

(73) Assignees: Teagasc, The Agriculture and Food Development Authority, Dublin (IE); National University of Ireland, Cork (IE)

( * ) Notice: Subject to any disclaimer, the term of this patent is extended or adjusted under 35 U.S.C. 154(b) by 0 days.

(21) Appl. No.: 09/720,382

(22) PCT Filed: Mar. 7, 2000

(86) PCT No.: PCT/IE99/00058

§ 371 (c)(1),
(2), (4) Date: Jun. 22, 1999

(87) PCT Pub. No.: WO99/67287

PCT Pub. Date: Dec. 29, 1999

(51) Int. Cl.$^7$ .................. A23L 3/3526; C12P 21/04
(52) U.S. Cl. .................. 426/335; 426/43; 426/532; 435/71.3
(58) Field of Search ................. 426/335, 532, 426/656, 34, 41, 42, 43; 424/282.1; 435/71.1, 71.3; 530/350

(56) References Cited

FOREIGN PATENT DOCUMENTS

DE    26 16 390    9/1974

OTHER PUBLICATIONS

McAuliffe, O., et al. (Feb. 1998) "Lacticin 3147, a Broad–Spectrum Bacteriocin Which Selectively Dissipates the Membrane Potential" *Appl. Environ. Microbiol.* 64(2):439–445.

Buzby, J.C. et al. (Aug. 1996) "Bacterial Foodborne Disease: Medical Costs & Productivity Losses. Food and Consumer Economics Division, Economic Research Service, U.S. Department of Agriculture" *Agricul. Econ. Rpt.* No. 741.

Coakley, M. et al. (Apr. 1997) "Application and Evaluation of the Phage Resistance– and Bacteriocin– Encoding Plasmid pMRC01 for the Improvement of Dairy Starter Cultures" *Appl. Environ. Microbiol.* 63(4):1434–1440.

Daeschel, M.A. (Jan. 1989) "Antimicrobial Substances from Lactic Acid Bacteria for Use as Food Preservatives" *Food Technol.* 43:164–167.

Dougherty, B., et al. (1998) "Sequence and Analysis of the 60 kb Conjugative, Bacteriocin–Producing Plasmid pMRC01 from Lactococcus Lactis DPC3147" *Mol. Microbiol.* 29(4):1029–1038.

Driessen, A.J.M., et al. (1995) "Mechanistic Studies of Lantibiotic–Induced Permeabilization of Phospholipid Vesicles" *Biochem.* 34:1606–1614.

García Garcerá, M.J., et al. (1993) "In Vitro Pore–Forming Activity of the Lantibiotic Nisin Role of Protonmotive Force and Lipid Composition" *Eur. J. Biochem.* 272:417–422.

Hurst, A. (1983) "Nisin and Other Inhibitory Substances from Lactic Acid Bacteria" *Antimicrobial in Foods* 10:327–351.

Joerger, M.C., et al. (1986) "Characterization and Purification of Helveticin J and Evidence for a Chromosomally Determined Bacteriocin Produced by *Lactobacillus helveticus* 481" *J. Bacteriol.* 167:439–446.

McAuliffe, O., et al. (1999) "Inhibition of Listeria Monocytogenes in Cottage Cheese Manufactured with a Lacticin 3147–producing Starter Culture" *J. Appl. Microbiol.* 86:251–256.

Muriana, P.M., et al. (Mar. 1987) "Conjugal Transfer of Plasmid–Encoded Determinants for Bacteriocin Production and Immunity in *Lactobacillus acidophilus* 88" *Appl. Environ. Microbiol.* 53(3):553–560.

Parente, E., et al. (1992) "A comparison of factors affecting the production of two bacteriocins from lactic acid bacteria" *J. Appl. Bacteriol.* 73:290–298.

Ryan, M.P., et al. (Feb. 1996) "An Application in Cheddar Cheese Manufacture for a Strain of *Lactococcus lactis* Producing a Novel Broad–Spectrum Bacteriocin, Lacticin 3147" *App. Environ. Microbiol.* 62(2):612–619.

Schillinger, U., et al. (1993) "Bacteriocin production by *Carnobacterium piscicola* LV 61" *Int. J. Food Microbiol.* 20:131–147.

Stiles, M.E. (1996) "Biopreservation by Lactic Acid Bacteria" *Antonie van Leeuwenhoek* 70:331–345.

Terzaghi, B.E., et al. (Jun. 1975) "Improved Medium for Lactic Streptococci and Their Bacteriophages" *Appl. Microbiol.* 29(6):807–813.

*Primary Examiner*—Keith Hendricks
(74) *Attorney, Agent, or Firm*—Antoinette F. Konski; Bingham McCutchen LLP

(57) ABSTRACT

The production of a spray-dried bacteriocin lacticin 3147 powder is described. The powder is shown to have effective anti-microbial activity in a range of foodstuffs, namely infant milk formulations, powdered soup, yoghurt and cottage cheese. Increased anti-microbial activity was demonstrated when the lacticin 3147 powder was used in conjunction with increased hydrostatic pressure. The process comprises: inoculating a medium with a lacticin 3147-producing strain of bacteria, fermenting the inoculated medium, adjusting the pH of the fermentation to 6.3–6.7, inactivating the bacterial fermentate and evaporating the fermentate.

14 Claims, 11 Drawing Sheets

Figure 1:
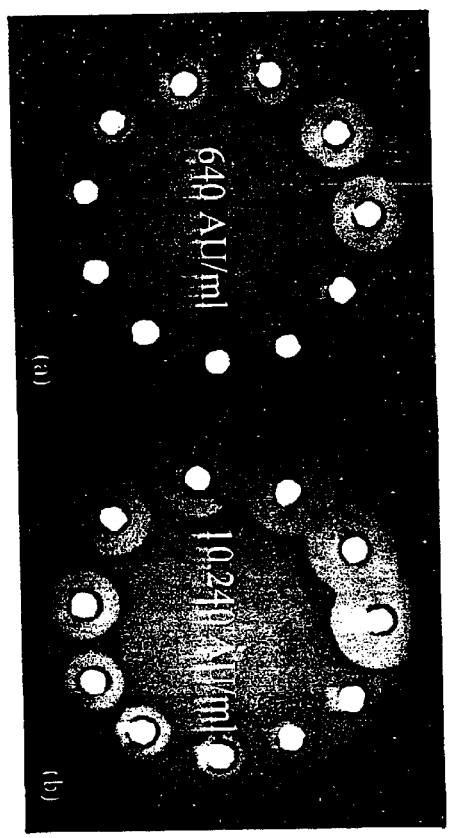
Figure 1:
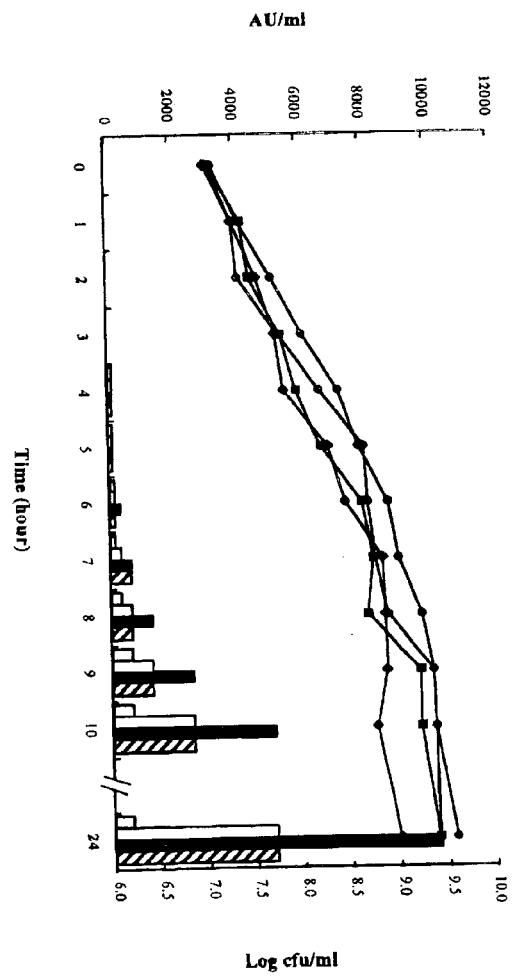

Effect of lacticin 3147 powder (10%) on the viability of *Listeria monocytogenes* Scott A in yogurt. (♦) no lacticin 3147 added, (■) 10% lacticin 3147 added.

The 10% here refers to 10g lacticin 3147 powder added to 90g yogurt.

Effect of lacticin 3147 powder (10%) on the viability of *Listeria monocytogenes* Scott A in cottage cheese. (♦) no lacticin 3147 added, (■) 10% lacticin 3147 added.

The 10% here refers to 10g lacticin 3147 powder added to 90g cottage cheese.

Soup - *Bacillus cereus*

Effect of lacticin 3147 powder (10%) on the viability of *Bacillus cereus* in (packet) soup.
(♦) no lacticin 3147 added,
(■) 1% lacticin 3147 added
(▲) 5% lacticin 3147 added
(●) 10% lacticin 3147 added The 1, 5, 10% here refers to 1, 5 or 10g lacticin 3147 powder added to 99, 95 or 90g packet soup powder, then reconstituted to the manufacturers instructions.

FIG. 8

Soup - *L. monocytogenes* Scott A

Effect of lacticin 3147 powder (10%) on the viability of *Listeria monocytogenes* ScottA in (packet) soup.
( ♦ ) no lacticin 3147 added,
( ■ ) 1% lacticin 3147 added
( ▲ ) 5% lacticin 3147 added
( ● ) 10% lacticin 3147 added The 1, 5, 10% here refers to 1, 5 or 10g lacticin 3147 powder added to 99, 95 or 90g packet soup powder, then reconstituted to the manufacturers instructions.

The effect of increasing pressures on the activity of lacticin 3147,
(a) atmospheric pressure, (b) 200 MPa, (c) 400 MPa, (d) 600 MPa and (e) 800 MPa.

The effect of high pressure and lacticin 3147 on *L. innocua* DPC1770 viability.

SPRAY-DRIED BACTERIOCIN POWDER WITH ANTI-MICROBIAL ACTIVITY

This application is a 371 of PCT/IE99/00058, filed Jun. 22, 1999.

The present invention relates to a spray-dried bacteriocin powder with anti-microbial activity, and to a method of producing the powder. In particular, the invention relates to a lacticin 3147 spray-dried powder.

1. Prior Art

The elimination of food spoilage and pathogenic organisms has become the focus of much research since, in terms of individuals affected and the cost of treatment, food-borne illnesses have an enormous impact. It has been estimated that microbial pathogens in food cause 6.5–33 million cases of human illness annually in the U.S., at a cost of between $2.9–$6.7 billion dollars (2), with Gram-positive food-borne pathogens accounting for between 25–55% of the costs. In recent years, consumer demand for fresh minimally processed safe food, in addition to concern over the use of chemical preservatives in foods, has prompted substantial interest in the application of biopreservatives. Bacteriocins produced by lactic acid bacteria are seen as alternatives to traditional preservatives for ensuring food safety and potential applications in foods have been readily identified (21).

Nisin, a bacteriocin produced by certain strains of Lactococcus lactis, has been used successfully to control food spoilage, in a number of different foods, including cheeses, canned goods and dairy desserts (10). However, its use is subject to certain restrictions. It is most effective in foods with acidic pH (below pH 6.0) and low protein and fat content. It is poorly soluble above pH 6.0 and as such has limited effectiveness in many foods. A powdered form of nisin, Nisaplin (Aplin and Barrett, Towbridge, Wiltshire, U.K.) has been developed and is used for the preservation of foods.

In addition to the development of Nisaplin, other powdered bacteriocin-containing agents have been developed for the preservation of foods. *Propionibacterium freundenreichii* subsp. shermanni is used to produce Microgard (Wesman Foods, Inc., Beaverton, Oreg.) by pasteurisation and drying of propionibacteria-fermented skim milk. It is estimated to be used in approximately one third of all cottage cheese made in the US and is said to be inhibitory to most Gram-negative bacteria and some fungi (4). The active agents in Microgard include propionic acid, acetic acid, diacetyl, lactic acid and a heat-stable peptide of approximately 700 daltons which is considered to be the most active component.

Lacticin 3147 is a bacteriocin produced by *L. lactis* DPC3147 which has a similar host range to that of nisin, in that it is inhibitory to a wide range of Gram-positive organisms, including Listeria, Clostridium spp., Enterococcus, Staphylococcus and Streptococcus (17). Given that many of these organisms have been identified as agents of food spoilage and pathogenesis, the development of a lacticin 3147-based system for control of these organisms has obvious attractions. This may be achieved in two ways. The first involves the use of starter cultures (including transconjugants) which produce lacticin 3147, and can be used in food fermentations where these strains can be substituted for the original starter cultures. The genetic determinants for lacticin 3147 are encoded on a 60.2 kb plasmid, pMRC01 which has been fully sequenced (6) and which has been mobilised to a number of cheese starter cultures (3). Lacticin 3147 is the subject of PCT Application No. PCT/IE96/00022, published as WO 96/32482.

Recently, it has been shown that a lacticin 3147 producing transconjugant can inhibit *Listeria monocytogenes* in Cottage cheese (13). This starter has also been used to control the proliferation of non-starter lactic acid bacteria in Cheddar cheese. The second approach to improving food safety through the use of lacticin 3147 involves the development of a spray-dried form of the bacteriocin. The advantage of such a bio-active powder is that it could be applied as a food ingredient in a variety of foods. However, it is not at all apparent that the bacteriocin is robust enough to withstand spray-drying and there was the possibility that spray-drying would result in a significant loss in bacteriocin activity.

OBJECT OF THE INVENTION

The object of the invention is to provide a lacticin 3147-enriched food ingredient for incorporation into foodstuffs. In particular, it is an object to provide a spray-dried lacticin 3147 powder. It could not be predicted that such a spray-dried powder could be produced since spray-drying could have caused heat denaturation of the bacteriocin, bearing in mind that lacticin 3147 is composed of two peptides, both of which are required for activity. Furthermore, dehydration could irreversibly inactivate the bacteriocin.

Described herein is a whey based bio-active powder, with effectiveness in controlling two representative pathogens, *L. monocytogenes* and *Staphylococcus aureus*, in buffer at both neutral and acidic pH. Also described is its effectiveness in controlling *L. monocytogenes* in an infant milk formulation and other foodstuffs. However, it will be apparent to those skilled in the art that the bacteriocin-powder of the invention need not be dairy based and that it would also be possible to produce a spray-dried bacteriocin based, for example, on other powders, synthetic materials or the like.

SUMMARY OF THE INVENTION

According to the present invention there is provided a process for the production of spray-dried lacticin 3147 powder comprising:

(a) inoculating a medium with a lacticin 3147-producing strain of bacteria;

(b) fermenting the inoculated medium;

(c) adjusting the pH of the fermentation to pH 6.3 to 6.7;

(d) inactivating the bacterial fermentate;

(e) evaporating the fermentate of step (d).

The medium which may be inoculated with the bacteria can be selected from milk or dairy-based powders including demineralised whey powder, reconstituted skimmed milk powder, whey protein concentrate powder, pasteurised milk, Cheddar cheese whey, or synthetic laboratory media such as LM17 or TY broth or the like.

Preferably the inoculated medium is fermented at about 30° C. for about 6 to 24 hours.

Preferably the pH of the fermentation is adjusted to about 6.5.

Suitably, the bacterial fermentate is inactivated by pasteurisation or treating at ultra-high temperature.

Suitably, if the fermentate is pasteurised, it is pasteurised at about 72° C. for about 15 seconds.

Preferably the inactivated fermentate is evaporated at about 60° C. to about 40% total solids.

The concentrate of step (e) may then be cooled to about 32° C., seeded with lactose at about 0.1% w/w and allowed to crystallise at a cooling rate of about 1° C. per hour.

The crystallised concentrate is then spray-dried by methods known in the art.

The invention also provides a spray-dried lacticin 3147 powder which has the ability to inhibit organisms which are not resistant to lacticin 3147 and which may suitably have an activity of about 40,240 au (arbitary units)/per ml.

The invention also provides a food product comprising a spray-dried lacticin 3147 powder as defined above. The food product may be an infant milk formulation, a sauce, mayonnaise, a dessert, a yoghurt, a custard, a tinned food product such as a tinned vegetable or tinned meat product, a soup, a bakery product or similar products.

The food product may further have been subjected to increased hydrostatic pressure during processing, suitably at a pressure of about 150 to 800 MPa.

FIGURE LEGENDS

The present invention will now be described in greater detail with reference to the accompanying drawings in which:

FIG. 1. (A) Growth of L. lactis DPC3147 and lacticin 3147 production in 10% reconstituted demineralized whey powder at 30° C., in pH controlled and uncontrolled conditions. (♦) cfu/ml with no pH control imposed, (■) cfu/ml at constant pH of 6.0, (●) cfu/ml at constant pH of 6.5 and (O) cfu/ml at constant pH of 7.0. (▨) AU/ml with no pH control, (□) AU/ml at constant pH of 6.0, (■) AU/ml at constant pH of 6.5 and (▨) AU/ml at constant pH of 7.0. (B) Inhibitory activity of lacticin 3147 against L. lactis HP when (a) grown with no pH control and when (b) grown at a constant pH of 6.5.

Figure 2:
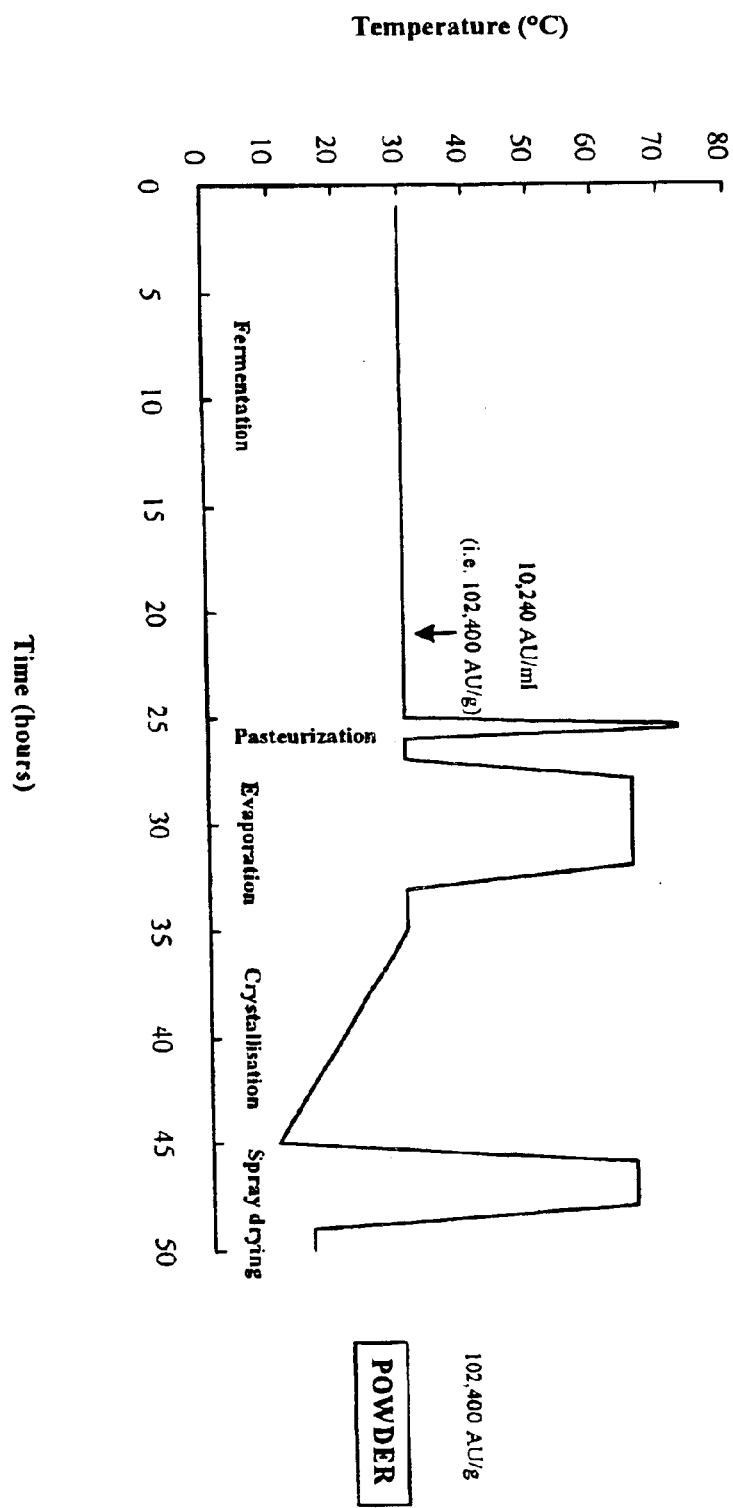

FIG. 2. Schematic diagram of temperature profile and lacticin 3147 activity during the manufacturing of lacticin 3147 powder.

Figure 3:
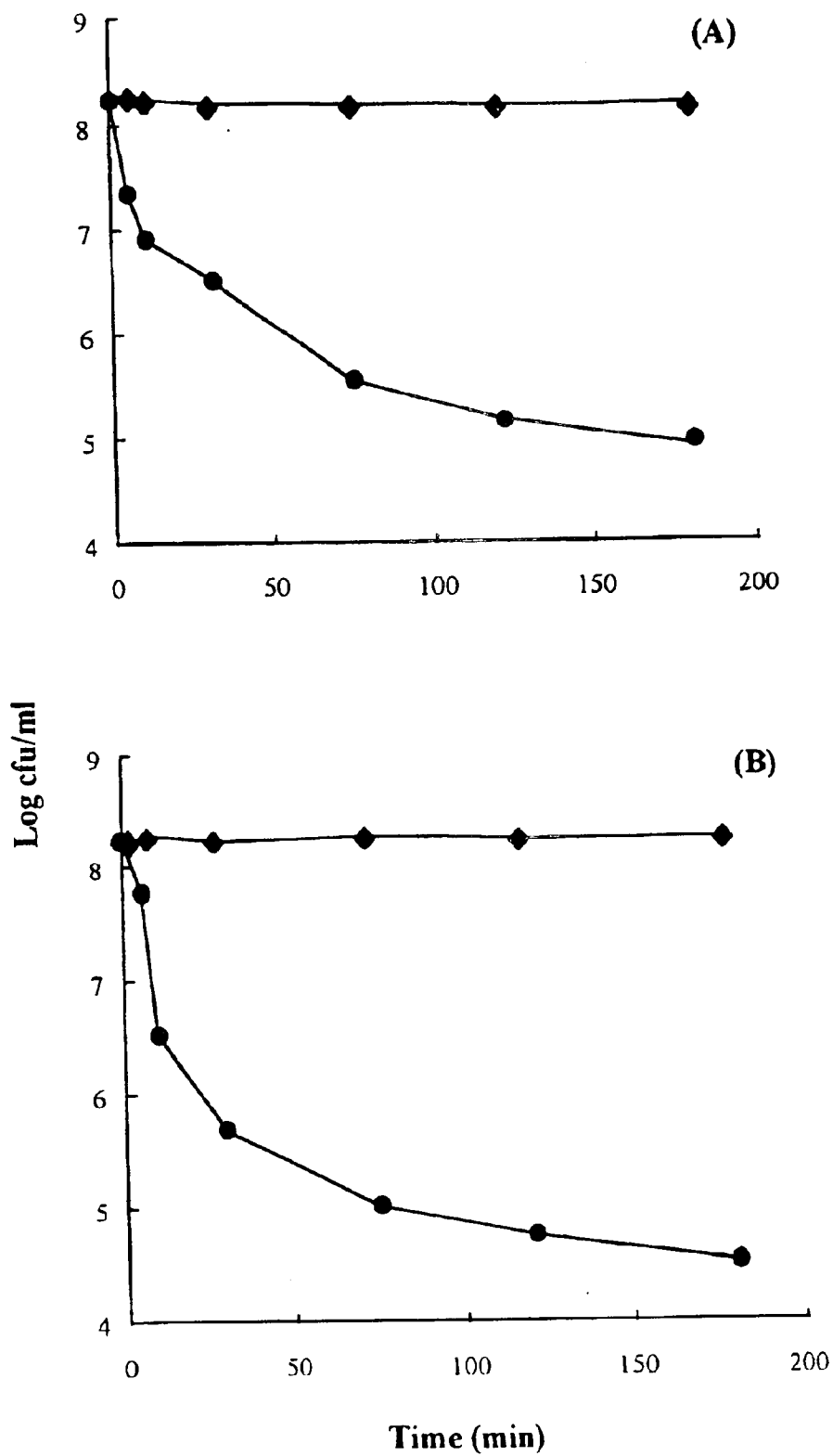

FIG. 3. Effect of lacticin 3147 powder on the viability of Listeria monocytogenes Scott A in buffer at 30° C. (A) at pH 5 and (B) at pH 7. (♦) no addition, (■) addition of 10% lacticin 3147 powder.

Figure 4:
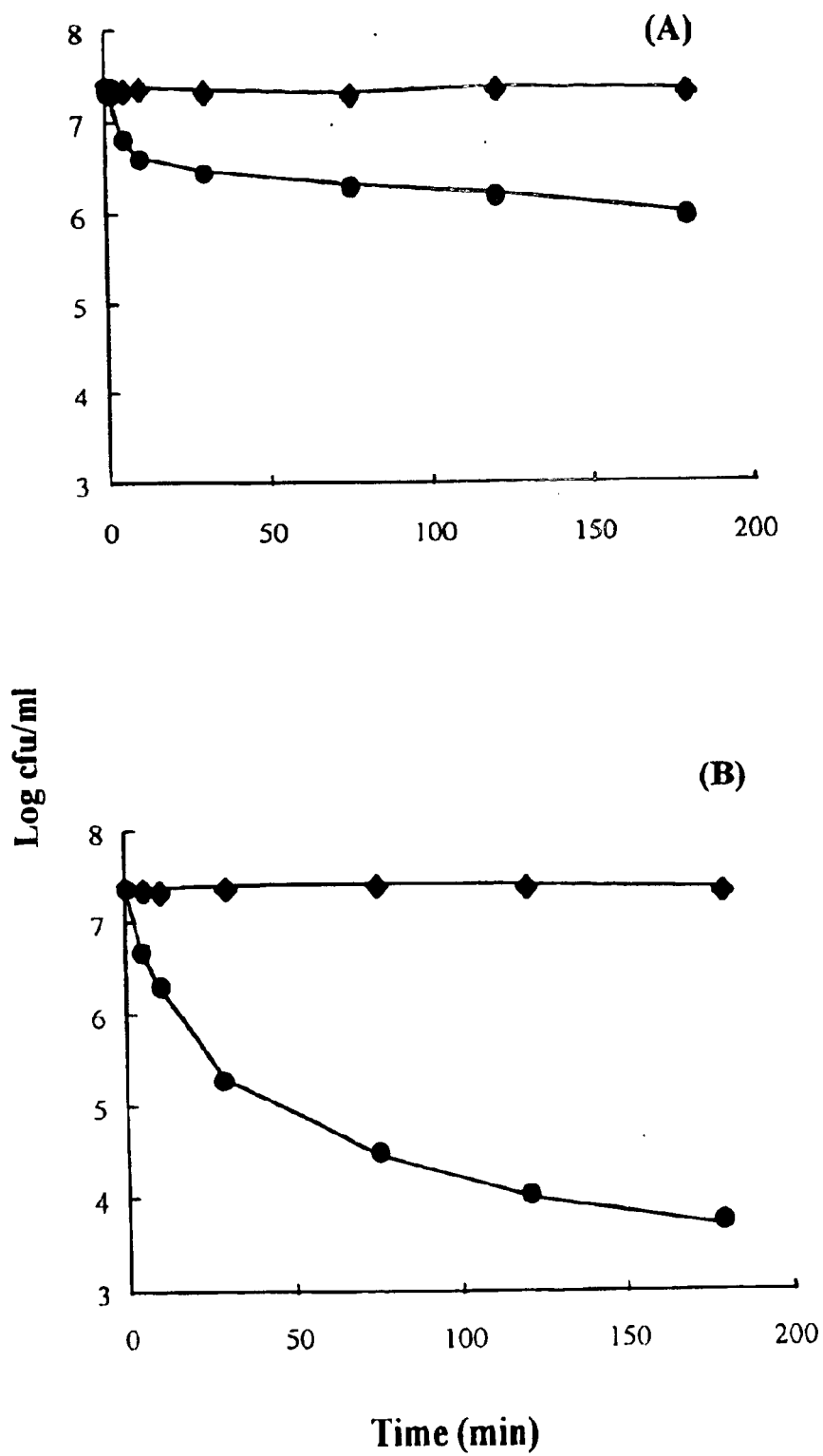

FIG. 4. Effect of lacticin 3147 powder on the viability of Staphylococcus aureus 10 in buffer at 30° C. (A) at pH 5 and (B) at pH 7. (♦) no addition, (■) addition of 15% lacticin 3147 powder.

Figure 5:
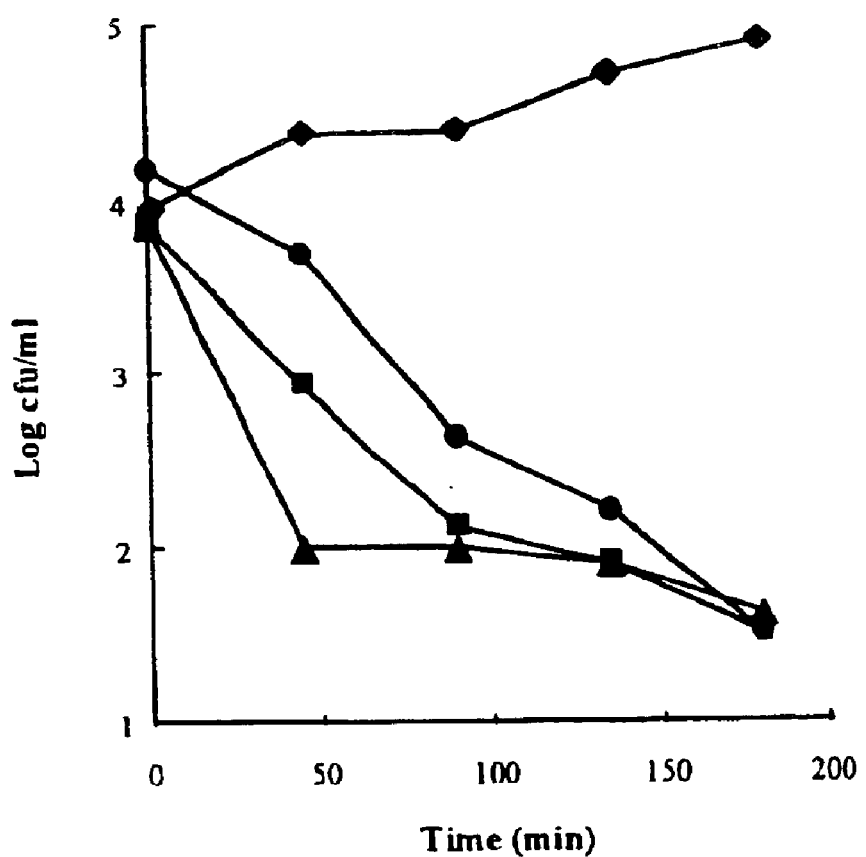

FIG. 5. Effect of lacticin 3147 powder on the viability of L. monocytogenes Scott A when used as a component of infant milk formula. (■) 15% lacticin powder, (▲) 10% lacticin powder, 5% infant milk powder, (●) 5% lacticin powder, 10% infant milk powder, (♦) 15% infant milk powder.

Figure 6:
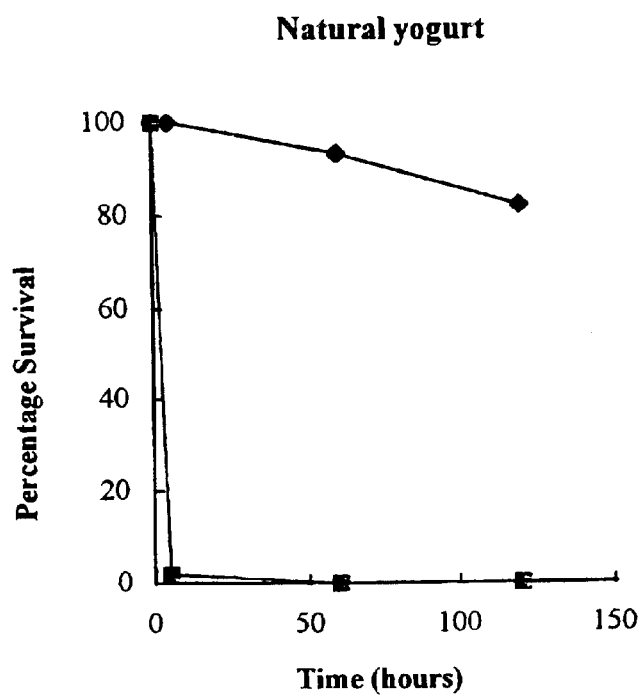

FIG. 6. Effect of lacticin 3147 powder (10%) on the viability of Listeria monocytogenes Scott A in yoghurt. (▲) no lacticin 3147 added, (■) 10% lacticin 3147 added. The 10% here refers to 10 g lacticin 3147 powder added to 90 g yoghurt.

Figure 7:
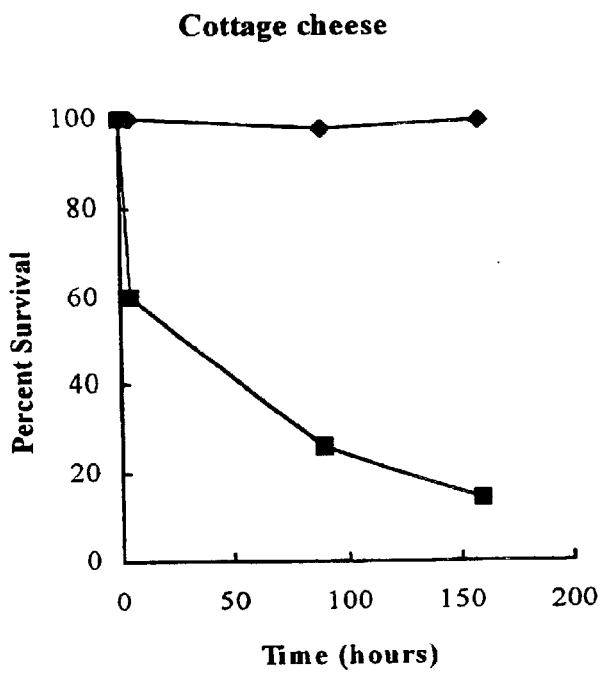

FIG. 7. Effect of lacticin 3147 powder (10%) on the viability of Listeria monocytogenes Scott A in cottage cheese. (♦) no lacticin 3147 added, (■) 10% lacticin 3147 added. The 10% here refers to 10 g lacticin 3147 powder added to 90 g cottage cheese.

FIG. 8. Effect of lacticin 3147 powder (10%) on the viability of Bacillus cereus in (packet) soup.
(♦) no lacticin 3147 added,
(■) 1% lacticin 3147 added,
(▲) 5% lacticin 3147 added,
(●) 10% lacticin 3147 added.

The 1, 5, 10% here refers to 1, 5 or 10 g lacticin 3147 powder added to 99, 95 or 90 g packet soup powder, then reconstituted to the manufacturers instructions.

Figure 9:
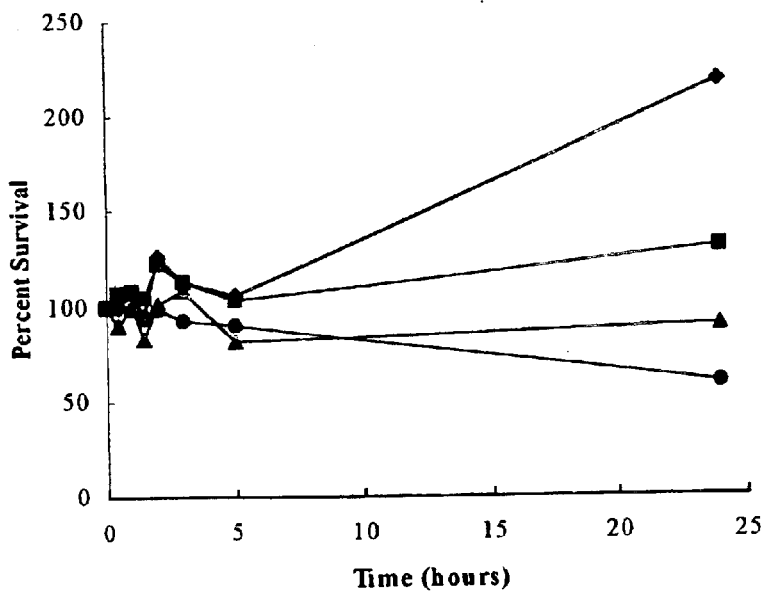

FIG. 9. Effect of lacticin 3147 powder (10%) on the viability of Listeria monocytogenes Scott A in (packet) soup.
(♦) no lacticin 3147 added,
(■) 1% lacticin 3147 added,
(▲) 5% lacticin 3147 added,
(●) 10% lacticin 3147 added.

The 1, 5, 10% here refers to 1, 5 or 10 g lacticin 3147 powder added to 99, 95 or 90 g packet soup powder, then reconstituted to the manufacturers instructions.

Figure 10:
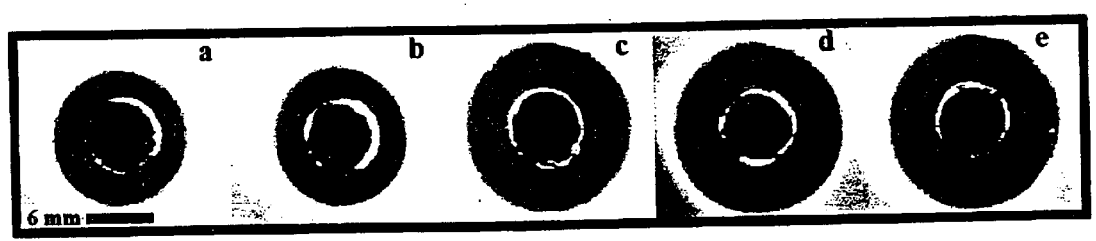

FIG. 10. The effect of increasing pressures on the activity of lacticin 3147, (a) atmospheric pressure, (b) 200 MPa. (c) 400 MPa, (d) 600 MPa and (e) 800 MPa.

Figure 11:
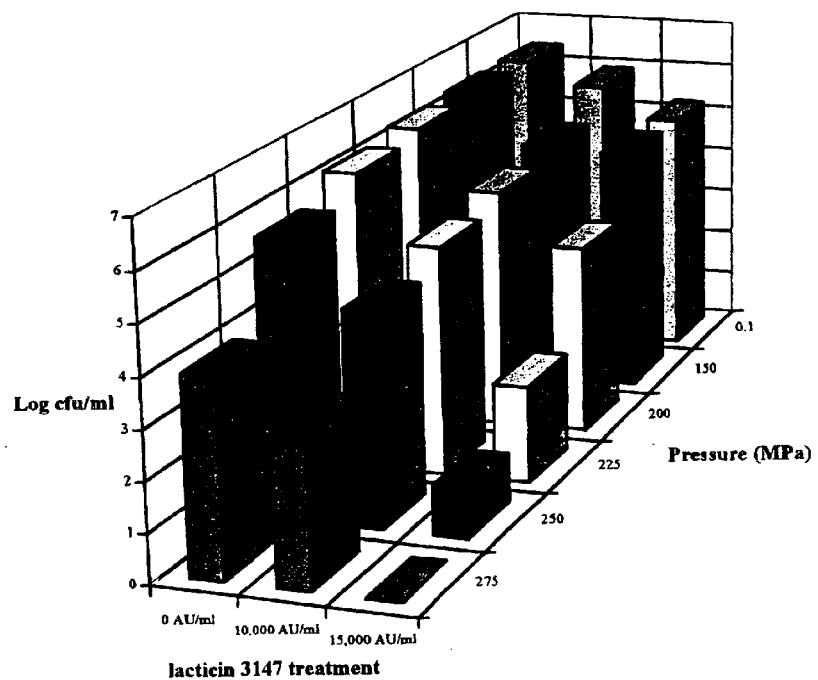

FIG. 11. The effect of high pressure and lacticin 3147 on L. innocua DPC1770 viability.

EXAMPLE

Material and Methods

Bacterial Strains and Culture Conditions

The bacteriocin producer L. lactis subsp lactis DPC3147 and the sensitive indicator strain L. lactis subsp lactis HP were routinely grown at 30° C. in M17 (20; Oxoid Ltd., Basingstoke, Hampshire, England) supplemented with 0.5% (w/v) lactose. Other indicator strains used included L. monocytogenes Scott A grown in Trypicase Soy Broth (TSB, Becton Dickinson and Co., Cockeysville, Md. 21030, USA) supplemented with 0.6% (w/v) yeast extract (Oxoid), and Staphylococcus aureus 10 (DPC culture collection, Moorepark, Fermoy, Co. Cork, Ireland) grown in Brain Heart Infusion broth (BHI, Oxoid), both at 37° C. Solid media was prepared by the addition of 1% bacteriological agar (Oxoid).

A number of different media were investigated for the production of lacticin 3147. These were made as 10% (w/v) solutions, apart from pasteurised whole milk and Cheddar cheese whey. The 10% solutions were prepared from demineralized whey powder (95% demineralized), reconstituted skimmed milk powder (Dairygold, Mitchelstown, Co. Cork, Ireland) and whey protein concentrate powder (WPC35, 35% protein in dry matter, Moorepark Technology Ltd., Moorepark, Fermoy, Co. Cork, Ireland). The whey based solutions were sterilised by heating to 95° C. for 30 minutes. The skimmed milk powder solution was sterilised by autoclaving for 5 min at 121° C.

Bacteriocin Assay and Activity Determination

Bacteriocin activity was determined by the agar well diffusion assay as described by Parente and Hill (15). Molten agar was seeded with an indicator strain and dispensed into petri dishes. Wells of approximately 4.6 mm in diameter were bored in the agar and a 50 μl volume of a two fold serial dilution of a bacteriocin preparation was dispensed into each well. Bacteriocin solution was prepared by centrifuging the culture and heat treating the supernatant at 70° C. for 10 minutes prior to carrying out the dilution series. The plates were then incubated at either 30° C. or 37° C., depending on the indicator strain used. Bacteriocin activity was calculated as the inverse of the last dilution that gave a definite zone of clearance after overnight incubation. Activity units (AU) were expressed per milliliter (1/dilution, ×20).

Controlled pH Fermentations.

Controlled pH fermentations were carried out over a 24 hour period, with slow agitation (approximately 20 rpm) at 30° C. A 1% inoculum of DPC3147 was used to inoculate 100 ml of growth media. The pH of the growth media was kept at a constant value by the addition of 1.0 M NaOH on demand via a 718 STAT Titrino (Metrohm, Ireland). Cell counts and bacteriocin activity determinations were carried out at hourly if intervals for the first 10 hours, and a final sample was taken after 24 hours.

Production of a Spray Dried Lacticin 3147 Powder.

A 170 L volume of demineralized whey powder (10% total solids) was inoculated with 1% DPC3147 and the pH of the 24 hour fermentation was controlled by the addition of 2.5M NaOH on demand (pH 6.5). The fermentate was then pasteurised at 72° C. for 15 sec using an APV SSP pasteurizer (APV, Silkborg, Denmark). The pasteurised fermentate was then evaporated at 60° C. to 40% total solids using a single effect falling film evaporator (Anhydro model F1 Lab). The resulting concentrate was cooled to 32° C., seeded with lactose (0.1% w/w) and allowed to pre-crystallize overnight at a cooling rate of 1° C. per hour. The pre-crystallized concentrate was then spray-dried using nozzle atomization in an Anhydro spray drier (Anhydro model Lab 3) at an air inlet temperature of 190° C. and a 90° C. outlet temperature. The powder was aliquoted, sachet packed in foil-lined sample bags and stored at 4° C. Bacteriocin activity was assessed at each step during the process.

Effect of Lacticin 3147 Powder Against Pathogens in Buffer

Sensitive cells were grown to mid-exponential phase, washed and resuspended at approximately $10^7$–$10^8$ cfu/ml in 2.5 mM sodium phosphate buffer, pH 7.0 or pH 5.0, and 2.5 mM sodium phosphate buffer, pH 7.0 or pH 5.0 supplemented with 10 mM glucose. Lacticin 3147 powder was added (at different concentrations depending on the sensitive strain under investigation) and samples were taken at appropriate time intervals over a 3 hour period to determine the viable cell count.

Effect of Lacticin 3147 Powder Against *L. monocytogenes* in an Infant Milk Formulation Lacticin 3147 powder was added to a commercially available infant milk formula, [ingredients listed as follows: demineralized whey powder, vegetable oils, lactose, skimmed milk, calcium carbonate, potassium citrate, calcium chloride, sodium citrate, magnesium chloride, vitamin C, emulsifier (soya lecithin), taurine, potassium hydroxide, iron sulphate, zinc sulphate, vitamin E, nicotinamide, pantothenic acid, vitamin A, copper sulphate, citric acid, thiamin, vitamin $B_6$, (carotene, manganese sulphate, potassium iodide, folic acid, vitamin K, sodium selenite, vitamin D, biotin). Manufacturers instructions indicate that the final liquid for infant consumption is a 15% solution (w/v). In experiments the 15% (w/v) infant milk powder was replaced with either 5% (w/v) lacticin powder and 10% (w/v) infant milk powder, or with 10% (w/v) lacticin powder and 5% (w/v) infant milk powder. *L. monocytogenes* cells were grown to mid-exponential phase, washed and resuspended at approximately $10^4$ cfu/ml in the various infant milk formulations at 30° C. and samples were taken at appropriate time intervals over a 3 hour period to determine the viable cell count.

Preparation of Lacticin 3147 for Use in High Pressure Inactivation Studies

For the inactivation of *Staph. aureus* ATCC6538 a liquid preparation of lacticin 3147 was prepared using hydrophobic adsorption chromatography. For studies on inactivation of *L. innocua* DPC1770 a food grade powdered preparation of lacticin 3147 was manufactured as described above with the following modification; a 1% demineralised whey powder solution was fermented with *L. lactis* subsp. lactis DPC3147 under pH controlled conditions of pH 6.0 for 18 hours.

Activity of both lacticin 3147 preparations was determined by the agar well diffusion assay as described by Parente and Hill (15). Molten agar was seeded with the indicator strain *L. lactis* subsp. lactis HP and dispensed into petri dishes. Wells of approximately 6.0 mm in diameter were bored in the agar and a 50 µl volume of a two fold serial dilution of a bacteriocin preparation was dispensed into each well. The plates were then incubated at 30° C. Bacteriocin activity was calculated as the inverse of the last dilution that gave a definite zone of clearance after overnight incubation. Activity units (AU) were expressed per milliliter (1/dilution, ×20). Activity may also be expressed as zone diameter (mm), where the diameter of the first zone (neat, undiluted sample) of the dilution series is recorded.

Effect of High Pressure on *Staph. aureus* ATCC6538 and *L. innocua* DPC1770 Viability

*Staph. aureus* ATCC6538 cells were resuspended in 10% RSM and aliquoted into sterile 700 µl PCR eppendorfs prior to placing in sterile stomacher bags (Seward Ltd., London, UK). Ten millilitre volumes of *L. innocua* DPC1770 cells were resuspended in 20% reconstituted demineralised whey powder aliquoted into sterile stomacher bags. Samples were individually vacuum sealed prior to placing in the pressure vessel (Stansted Fluid Power Ltd., Stansted, England). The vessel consisted of a stainless-steel cylinder (37 mm diameter×300 mm height) filled with a 15% (v/v) caster oil in ethanol solution which acts as the hydrostatic pressurisation medium. Samples were treated for 30 min at 25° C. in the pressure range 150 to 600 MPa, in addition to a control sample being held at atmospheric pressure (0.1 MPa). All experiments were carried out in duplicate. The chamber temperature was determined by means of a thermoregulating system which circulated to maintain the chamber temperature.

Effect of High Pressure on Lacticin 3147 Activity

To determine the effect of high pressure on lacticin 3147 activity, reconstituted lacticin 3147 powder and aliquots of liquid lacticin 3147 were vacuum sealed and exposed to pressures ranging from 100 to 800 Mpa as described above. Pressurised and non-pressurised solutions of lacticin 3147 were heat treated at 80° C. for 10 minutes prior to carrying out activity determination by the well diffusion assay using *L. lactis* HP as an indicator strain.

Results

The objective of this research was to develop a powdered form of lacticin 3147 suitable for use as an ingredient which could help in the control of undesirable micro-organisms in foods. Following the optimization of lacticin 3147 production a scale-up fermentation was carried out and the fermentate was spray-dried to form a bacteriocin-rich powder. This powder was assessed in both a buffer and an infant milk food system for it, ability to inhibit pathogens.

Lacticin 3147 Production in Various Media

Following inoculation of DPC3147 (1%) and overnight incubation at 30° C., lacticin 3147 activity was assessed in a number of different growth media. Most of the media were dairy based, but two synthetic media were also included (LM17 and TY). Results of production of lacticin 3147 (see Table 1) demonstrated that activity was high in almost all the dairy based media (1,280 to 2,560 AU/ml) apart from WPC35 (320 AU/ml). Highest levels of lacticin 3147 activity were found in Cheddar cheese whey, whole milk and LM17 (2,560 AU/ml). Both 10% reconstituted demineralized whey powder and 10% reconstituted skimmed milk powder gave activity of 1,280 AU/ml. Lower levels of lacticin 3147 activity were observed in TY broth (640 AU/ml).

Since demineralized whey powder is a commercially and readily available, and good lacticin 3147 activity was observed in this media, further investigations into the optimization of lacticin 3147 production in demineralized whey powder was carried out.

Optimization of Lacticin 3147 Production in 10% Reconstituted Demineralized Whey Powder Bacteriocin production and viable cell counts in pH-controlled and pH-uncontrolled fermentations revealed that increased levels of lacticin 3147 could be produced by maintaining the pH of the growth media constant, at pH 6.5 (FIG. 1). Levels of bacteriocin activity reached 10,240 AU/ml in 10% reconstituted demineralized whey powder when the pH of the growth media was held constant at pH 6.5 (FIG. 1B($a$)) compared to 640 AU/ml when no pH control was imposed (FIG. 1B($b$)). At both pH 6.0 and pH 7.0 lacticin activity reached 5120 AU/ml. Results of viable cell counts over a 24 hour period indicated that increased bacteriocin activity corresponded to higher cell densities. Without pH control viable cell counts reached $1\times10^9$ cfu/ml, whereas when the pH of the growth media was maintained at a constant pH of 6.5 viable cell counts reached $3.8\times10^9$ cfu/ml (FIG. 1A). With pH control at 6.0 and 7.0 viable cell counts reached $2.5\times10^9$ cfu/ml.

Production of Lacticin 3147 Powder

A spray-dried lacticin 3147 preparation was manufactured as described in materials and methods. During the manufacturing process bacteriocin activity was assessed at each step, using $L.$ $lactis$ HP as the indicator strain (FIG. 2). Following the pH controlled fermentation (in 10% reconstituted demineralized whey powder) bacteriocin activity was 10,240 AU/ml. The fermentate was subjected to pasteurisation to inactivate the bacteriocin producing culture DPC3147. Pasteurisation had no effect on bacteriocin activity (FIG. 2). Evaporation (from 10% total solids to 40% total solids) led to a concentration of the fermentate and resulted in an increase in bacteriocin activity to 40,960 AU/ml. Following overnight crystallisation, the activity of the concentrate remained stable. Spray drying of the concentrate resulted in the production of an active powder. When resuspended at a concentration of 50 mg/ml (5% solids) the spray dried powder contained 5,120 AU indicating that the activity of the lacticin powder was 102,400 AU/g (100% solids). Lacticin 3147 activity expressed as AU/g of dry matter remained constant throughout manufacture at 102, 400 AU/g, indicating that no loss in bacteriocin activity occurred during processing.

The inhibitory activity of the bacteriocin-enriched powder was attributed to the action of lacticin 3147 rather than other fermentation metabolites such as lactic acid, since it inhibited a sensitive $L.$ $lactis$ MG1614, but did not show any inhibitory effect against a transconjugant containing the pMRC01 plasmid.

Effect of Lacticin 3147 Powder on Pathogens

The lacticin 3147 enriched demineralized whey powder (lacticin 3147 powder) was investigated for its ability to inhibit two food-borne pathogens. The inhibitory effect of the powder was investigated at pH 5 and at pH 7, in the presence and absence of 10 mM glucose. The effectiveness of a 10% (w/v) solution of lacticin 3147 powder against mid-exponential growth phase cells of $L.$ $monocytogenes$ Scott A demonstrated that approximately a 3.3 log kill (99.95% kill) could be achieved at pH 5 within 3 hours at 30° C. (FIG. 3A). Killing of $L.$ $monocytogenes$ Scott A with a 10% (w/v) solution of lacticin powder was slightly more effective at pH 7 (FIG. 3B). A 3.8 log kill (99.98% kill) was observed within 3 hours at 30° C.

$S.$ $aureus$ 10 was found to be more resistant than $L.$ $monocytogenes$ Scott A to the action of the lacticin enriched powder, for this reason a 15% solution of the powder was used. The effectiveness of a 15% (w/v) solution of lacticin 3147 powder against mid-exponential phase cells of $S.$ $aureus$ 10 resulted in approximately a 1.1 log kill (90.4% kill) at pH 5 within 3 hours at 30° C. (FIG. 4A). The killing effect of a 15% solution (w/v) of lacticin powder increased dramatically at pH 7, where almost a 4 log kill (99.98% kill) of $S.$ $aureus$ 10 was observed within 3 hours at 30° C. (FIG. 4B). The inclusion of 10 mM glucose resulted only slight increases in the level of cell deaths for either $L.$ $monocytogenes$ Scott A or $S.$ $aureus$ 10 (results not shown).

Effect of Lacticin 3147 Powder Against $L.$ $monocytogenes$ Scott A in an Infant Milk Formulation To evaluate the effectiveness of the lacticin 3147 powder in a food system experiments were carried out in an infant milk formula, since this is an example of a food destined for a high-risk consumer which contains demineralized whey powder as a major constituent. Results indicated greater that a 99% kill of $L.$ $monocytogenes$ Scott A resulted when part of the infant milk formulation was substituted with either two thirds (10% lacticin powder and 5% infant milk powder) or one third lacticin 3147 powder (5% lacticin powder and 10% infant milk powder) (FIG. 5). Counts here were reduced from approximately $7\times10^4$ cfu/ml to $3\times10^1$ cfu/ml within 3 hours at 30° C. In the control culture with no lacticin 3147 powder present counts increased from approximately $10^4$ cfu/ml to approximately $10^5$ cfu/ml within the same time period.

Application of Lacticin 3147 Powder in a Range of Foods

Powdered lacticin 3147 has been assessed for the inhibition of food spoilage and pathogenic micro-organisms in a number of food systems including infant food formula, powdered soup, cottage cheese and natural yoghurt. The following are specific examples of the use of lacticin 3147 to inhibit pathogens in food systems.

The ability of the lacticin 3147 powder to inhibit $Listeria$ $monocytogenes$ Scott A was initially investigated in an infant milk formulation as described above. To further investigate the inhibitory effect of the lacticin 3147 powder, inactivation trials were carried out against a number of different micro-organisms in natural yoghurt, cottage cheese and reconstituted powdered soup, with pHs of 4.5, 4.4 and 6.6 respectively.

The effect of 10% lacticin 3147 powder on the inhibition of $Listeria$ $monocytogenes$ Scott A ($10^4$ cfu/ml) in natural yoghurt demonstrated that greater than 98.3% of the culture was killed within 5 minutes at 30° C. Within 60 minutes no viable cells remained, (FIG. 6).

In the case of cottage cheese inoculated with $10^4$ cfu/ml $Listeria$ $monocytogenes$ 40% of the population was killed within 5 minutes at 30° C. in the presence of a 10% lacticin 3147 powder. After 160 minutes only 14% of the population remained viable, (FIG. 7).

The effect of 1, 5 and 10% concentrations of lacticin 3147 in powdered soup against $Bacillus$ $cereus$ at 30° C., demonstrated that following 24 hours incubation greater than a 99.9% kill was observed in the presence of the 5 and 10% lacticin 3147 powder concentrations. In the case of the 1% lacticin 3147 concentration 17% of the population survived, (FIG. 8).

A similar study was carried out to determine the effect of 1, 5 and 10% concentrations of lacticin 3147 powder on the survival of $Listeria$ $monocytogenes$ Scott A in powdered soup. A 1% concentration of lacticin was ineffective at inhibiting Scott A within 24 hours, whereas at a 5% concentration greater than 10% of the population were inhibited. At a concentration of 10% greater than 40% of the culture was inhibited, (FIG. 9).

From these results it can be seen that a powdered form of lacticin 3147 has indeed many applications in food safety for the control of food pathogens and spoilage organisms.

Effect of Hydrostatic Pressure

The use of hydrostatic pressure and lacticin 3147 treatments were evaluated in milk and whey with a view to combining both treatments for improving the quality of minimally processed dairy foods. The system was evaluated using two foodborne pathogens, *Staphylococcus aureus* ATCC6538 and *Listeria innocua* DPC1770. Trials against *Staph. aureus* ATCC6538 were performed using concentrated lacticin 3147 prepared from culture supernatant. Results demonstrated greater than an additive effect when both treatments were used in combination, for example, the combination of 250 MPa (2.2 log reduction) and lacticin 3147 (1 log reduction) resulted in more than 6 logs of kill (FIG. 10). Similar results were obtained when a foodgrade powdered form of lacticin 3147 (developed from a spray dried fermentation of reconstituted demineralised whey powder) was evaluated for the inactivation of *L. innocua* DPC1770 (FIG. 11). Furthermore, it was observed that treatment of lacticin 3147 preparations with pressures greater than 400 MPa yielded an increase in bacteriocin activity (equivalent to a doubling of activity). These results indicate that a combination of high pressure and lacticin 3147 may be suitable for improving the quality of minimally processed foods at lower hydrostatic pressure levels.

Discussion

The development of a whey based bio-active food ingredient was achieved following investigations into lacticin 3147 production in different media. Lacticin 3147 activity was high in all of the dairy based media investigated, apart from whey protein concentrate (WPC35). A possible explanation for the low level of activity in the whey protein concentrate could be that bacteriocin activity fractionated into the pellet upon centrifugation, prior to assaying for activity. Two synthetic media were investigated for lacticin 3147 production, LM17 broth (20) and TY broth (15). Levels of lacticin 3147 activity in LM17 were comparable to dairy based media, but this is not unexpected, since this media was developed for the cultivation of lactococci. However, TY broth, in which low levels of lacticin 3147 activity was observed, was developed to yield optimal bacteriocin (enterocin 1146) production while minimising peptide levels in the medium (to eliminate peptides that may interfere with purification). For the development of a powder the use of the most cost effective growth media is obviously advantageous. Demineralized whey powder, a readily available and cost effective medium ($20 per 25 Kg) was investigated for the optimization of lacticin 3147 production. However, other suitable growth media could be used, as described above.

The effect of pH on bacteriocin production has been well documented, and for a number of bacteriocin-producing strains control of pH during growth results in higher bacteriocin titres (11, 14, 18). Lacticin 3147 activity increased dramatically when the pH of the growth media was held constant at pH 6.5, 5 highest bacteriocin titres and highest cell numbers were observed at this pH. Lowest bacteriocin titres and lowest cell numbers were observed when no pH control was imposed. Increased bacteriocin activity corresponded with increased cell numbers.

Once lacticin 3147 production had been optimized in 10% reconstituted demineralized whey powder a large-scale fermentation was set up to generate enough fermentate for spray drying. The production of an active spray dried powder demonstrated the resilience of the bacteriocin, to the extremes of the processing conditions. Activity was detected throughout the process and the final powder had an activity of 102,400 AU/g dry matter, equivalent to the activity present at the beginning of the process. This unexpected result is significant in that it suggests that no loss in activity occurred during production.

Assessment of the inhibitory activity of the bio-active powder demonstrated that it is capable of inhibiting both *L. monocytogenes* and *S. aureus* at pH 5 and at pH 7. In both cases the bio-active powder exhibited enhanced killing ability at neutral pH. This is a significant finding, since Nisaplin, a fermented food ingredient for extension of product shelf life and prevention of spoilage is known to be most effective at acidic pH (below pH 6.0). The development of a food ingredient capable of killing Gram-positive bacteria at neutral pH indicates that the lacticin 3147 powder may be suitable for incorporation into a wide range of foods, that hitherto had no opportunity for the prevention of food spoilage/pathogenesis apart from the inclusion of chemical preservatives.

The mechanism of action of lacticin 3147 has been elucidated (12). It induces cell death by permeabilising the membranes of sensitive cells through pore formation, allowing the efflux of $K^+$ ions and phosphate. This action results in the dissipation of the proton motive force, hydrolysis of intracellular ATP and ultimately leads to cell death. Energised cells are more susceptible to the action of lacticin 3147. Cells incubated in the presence of lacticin powder combined with 10 mM glucose demonstrated slight increases in killing efficiency (apart from *S. aureus* 10 at pH 7, results not shown). This is in keeping with results reported by McAuliffe et al., (12), where energised cells were observed to be more sensitive to lacticin 3147. Energised cells have a proton motive force which may favour the insertion of lacticin 3147 molecules into the membrane, as is the case with nisin, a lantibiotic pore former (7, 8).

The development of a powdered form of lacticin 3147 would allow it to be applied to a number of food systems. Since the existing lacticin 3147 powder has been developed from a demineralized whey powder, this powder has applications in all foods where demineralized whey powder is an existing ingredient. For example demineralized whey powder is incorporated into a number of foods including infant milk formulations. Results presented in this paper demonstrate the ability of this powder to effectively inactivate 99% of *L. monocytogenes* Scott A spiked into infant formula, where part of the infant milk powder had been substituted with the lacticin 3147 powder. Infant milk formulations are manufactured to the highest of standards and incidents of food-borne illness associated with such foods are rare. However more than many other foods infant milk formulas are susceptible to contamination through domestic contamination, putting the health of infants at risk. For this reason the inclusion of a lacticin 3147 enriched powder in such formulations may offer increased protection in the event of contamination, which would be beneficial to both producers and consumers.

For manufacturers already using demineralized whey powder as a food ingredient it should prove possible to substitute this powder (either partially or fully) with a bio-active demineralized whey powder to further safe guard food products from spoilage and pathogenic Gram-positive organisms. And indeed, for manufacturers who do not use demineralized whey powder as a food ingredient the inclusion of low levels of the bio-active powder could be sufficient to confer enhanced protection without affecting the sensory or functional characteristics of these foods. It is, however, also apparent that a spray-dried lacticin 3147 powder based on a medium other than whey powder, would be obtainable by this invention. Such a powder has potential for application as a substitute in areas where whey powder is not utilised, with the same beneficial effects.

SUMMARY

The broad-spectrum bacteriocin lacticin 3147, produced by Lactococcus lactis DPC3147, is inhibitory to a wide range of Gram-positive food spoilage and pathogenic organisms. A 10% solution of demineralized whey powder was fermented with DPC3147 at a constant pH of 6.5. The fermentate was spray dried and the resulting powder exhibited inhibitory activity. The ability of the lacticin 3147-enriched powder to inhibit Listeria monocytogenes Scott A and Staphylococcus aureus 10 was assessed in buffer at both acidic (pH 5) and neutral pH (pH 7). In addition, the ability of the powder to inhibit L. monocytogenes Scott A in an infant milk formulation was assessed. Resuspension of 8.3 log mid-exponential phase L. monocytogenes Scott A cells in a 10% solution of the lacticin 3147-enriched powder resulted in a 1000 fold reduction in viable cells at pH 5 and pH 7, after 3 hours at 30° C. In the case of S. aureus 10, resuspension of $2.5 \times 10^7$ mid-exponential phase cells in a 15% solution of the lacticin 3147-enriched powder at pH 5 resulted in only a 10 fold reduction in viable cell counts, compared to a 1000 fold reduction at pH 7, following incubation for 3 hours at 30° C. In an infant milk formulation the use of the lacticin 3147 powder resulted in greater than a 99% kill of L. monocytogenes within 3 hours at 30° C. Similarily, the lacticin 3147 powder was shown to be effective in inhibiting food spoilage in powdered soup, yoghurt and cottage cheese. Furthermore, the combination of hydrostatic pressure and lacticin 3147 causes increased killing making this an attractive method of preventing spoilage in minimally processed foodstuffs. Thus this bioactive lacticin 3147 food ingredient will find applications in many different foods, including those with pH close to neutrality.

References

2. Buzby, J. C., T. Roberts, C. T. J. Lin, and J. M. MacDonald. 1996. Bacterial Food-borne Disease: Medical Costs and Productivity Losses. Food and consumer economics division, economic research service, U.S. Department of Agriculture. Agricultural Economic Report No. 741.
3. Coakley, M., G. F. Fitzgerald and R. P. Ross. 1997. Application and evaluation of the phage resistance and bacteriocin-encoding plasmid pMRC01 for the improvement of dairy starter cultures. Appl. Environ. Microbiol. 63:1434–1440
4. Daeschel, M. A. 1989. Antimicrobial substances from lactic acid bacteria for use as food preservatives. Food Technol. 43:164–167
6. Dougherty, B., C. Hill, J. F. Weidman, D. R. Richardson, J. C. Venter and R. P. Ross. Sequence and analysis of the 60 kb conjugative, bacteriocin producing plasmid pMRC01 from Lactococcus lactis DPC3147. Mol. Microbiol. (in press).
7. Driessen, A. J. M., H. W. van der Hooven, W. Kuiper, M. van de Kamp, H.-G. Sahl, R. N. H. Konings, and W. N. Konings. 1995. Mechanistic studies of lantibiotic-induced permeabilisation of phospholipid vesicles. Biochem. 34:1606–1614.
8. Garcia-Garcera, M. J., M. G. M. Elferink, A. J. M. Driessen, and W. N. Konings. 1993. In vitro pore-forming activity of the lantibiotic nisin: role of protonmotive-force and lipid composition. Eur. J. Biochem. 212:417–422.
10. Hurst, A. 1983. Nisin and other inhibitory substances from lactic acid bacteria, p. 327–351. In P. M. Davidson and A. L. Branen, (ed.), Antimicrobials in food, Marcel Dekker, New York.
11. Joerger, M. C., and T. R Klaenhammer. 1986. Characterization and purification of helveticin J and evidence for a chromosomally determined bacteriocin produced by Lactobacillus helveticus 481. J. Bacteriol. 167:439–446
12. McAuliffe, O., M. P. Ryan, R. P. Ross, C. Hill, P. Breeuwer and T. Abee. 1998. Lacticin 3147: a broad spectrum bacteriocin which selectively dissipates the membrane potential. Appl. Environ. Microbiol. 64:439–445.
13. McAuliffe, O., C. Hill and R. P Ross. 1998. Inhibition of Listeria monocytogenes in Cottage cheese manufactured with a lacticin 3147 producing starter culture. Submitted for publication: J. Appl. Microbiol.
14. Muriana, P. M., and T. R. Klaenhammer. 1987. Conjugal transfer of plasmid encoded determinants for bacteriocin production and immunity in Lactobacillus acidophilus 88. Appl. Environ. Microbiol. 53:553–560.
15. Parente, E., and C. Hill. 1992. A comparison of factors affecting the production of two bacteriocins from lactic acid bacteria. J. Appl. Bacteriol. 73:290–298.
17. Ryan, M. P., M. C. Rea, C. Hill and R. P. Ross. 1996. An application in Cheddar cheese manufacture for a strain of Lactococcus lactis producing a novel broad-spectrum bacteriocin, lacticin 3147. Appl. Environ. Microbiol. 62:612–619.
18. Schillinger, U., M. E. Stiles, and W. H. Holzapfel. 1993. Bacteriocin production by Carnobacterium piscicola LV61. Int. J. Food Microbiol. 20:131–147.
20. Terzaghi, B. E., and W. E. Sandine. 1975. Improved medium for lactic streptococci and their bacteriophages. Appl. Environ. Microbiol. 29:807–813.
21. Stiles, M. E. 1996. Biopreservation of lactic acid bacteria. In lactic acid bacteria: genetics, metabolism and applications (Venema, G., huis in't Veld, J. H. J. and Hugenholz, J. eds.) Proceedings of the Fifth Symposium, veldhoven, the Netherlands, 235–249, Kluwer Academic Publishers.

The words "comprises/comprising" and the words "having/including" when used herein with reference to the present invention are used to specify the presence of stated features, integers, steps or components but does not preclude the presence or addition of one or more other features, integers, steps, components or groups thereof.

TABLE 1

Lacticin 3147 activity in various media after overnight incubation at 30° C.

| Growth Media | Lacticin 3147 activity (AU/ml) |
| --- | --- |
| Cheddar cheese whey | 2560 |
| Whole milk | 2560 |
| Reconstituted skimmed milk powder | 1280 |
| Reconstituted demineralised whey powder | 1280 |
| Whey protein concentrate (WPC3S) | 320 |
| LM17 | 2560 |
| TY broth | 640 |

What is claimed is:
1. A process for the production of a spray-dried concentrate comprising lacticin 3147, for use as a food ingredient, comprising:

(a) inoculating a milk or dairy based medium with a lacticin 3147-producing strain of bacteria;

(b) fermenting the inoculated medium;

(c) adjusting the pH of the fermentation to a pH ranging from 6.3 to 6.7;

(d) inactivating the bacteria within the fermentate; and (e) evaporating the fermentate of step (d) thereby producing the lacticin 3147 concentrate for use as a food ingredient.

2. A process as claimed in claim 1, wherein the medium of step (a) is selected from the group consisting of milk, reconstituted dairy-based powders, reconstituted demineralized whey powder, reconstituted skimmed milk powder, reconstituted whey protein concentrate powder, pasteurized whole milk, Cheddar cheese whey, reconstituted yeast powders, and synthetic laboratory-type media.

3. A process as claimed in claim 1 or 2, wherein the evaporation step of step (e) comprises cooling the fermentate of step (d), seeding it with lactose at about 0.1% w/w and crystallizing at a cooling rate of about 1° C. per hour.

4. A process as in claim 1, wherein the inoculated medium of step (b) is fermented at about 30° C. for about 6 to 24 hours.

5. A process as in claim 1, wherein the pH of the fermentation is adjusted in step (c) to about pH 6.5.

6. A process as in claim 1, wherein the fermentate of step (d) is inactivated by pasteurization or ultra-high temperature treatment.

7. A process as claimed in claim 6, wherein said pasteurization step comprises heating at about 72° C. for about 15 minutes.

8. A process as in claim 1, wherein step (e) comprises evaporating said bacteria fermentate at about 60° C. to about 40% total solids.

9. A process as in claim 1, further comprising the step of spray-drying the concentrate.

10. A concentrate comprising a food-grade spray-dried lacticin 3147 produced by the process of any one of claims 1 to 9.

11. A spray-dried food-grade powder containing lacticin 3147 having the ability to inhibit organisms which are not resistant to lacticin 3147, and having an activity of greater than about 20,000 AU/ml.

12. A food product comprising a lacticin 3147 enriched spray-dried food-grade fermentate produced by the process of any one of claims 1 to 9 and a foodstuff.

13. The food product as claimed in claim 12, wherein said product is selected from the group consisting of an infant milk formulation, a sauce, a mayonnaise, a dessert including a custard, a tinned food, a yogurt, a soup and a bakery product.

14. A food product as claimed in claim 12 or 13, which has been subjected to hydrostatic pressure in the range from about 150 MPa to about 800 MPa.

* * * * *

UNITED STATES PATENT AND TRADEMARK OFFICE
CERTIFICATE OF CORRECTION

PATENT NO.    : 6,833,150 B1
DATED         : December 21, 2005
INVENTOR(S)   : Reynolds Paul Ross It is certified that error appears in the above-identified patent and that said Letters Patent is hereby corrected as shown below:

Title page,
Item [22], PCT Filed, delete "Mar. 7, 2000" and insert -- Jun. 22, 1999; --
Item [86], PCT No. § 371(c)(1), (2), (4) Date delete "Jun. 22, 1999" and insert -- Mar. 7, 2001; --

Column 13,
Line 1, before "milk" insert -- food grade; --
Line 15, after "whey" delete ", reconstituted yeast powders, and synthetic laboratory-type media;"

Column 14,
Line 16, before "powder", insert -- milk or dairy based; --
Line 25, after "dessert" delete -- including a custard --

Signed and Sealed this

Twenty-eighth Day of June, 2005

JON W. DUDAS
*Director of the United States Patent and Trademark Office*